United States Patent [19]

Freyer et al.

[11] Patent Number: 5,030,753
[45] Date of Patent: Jul. 9, 1991

[54] PROCESS FOR THE PREPARATION OF DICHLORO- OR TRICHLOROACETYL CHLORIDE

[75] Inventors: Walter Freyer, Leitershofen; Karlheinz Miltenberger, Gersthofen; Manfred Schmidt, Günzburg, all of Fed. Rep. of Germany

[73] Assignee: Hoechst Aktiengesellschaft, Frankfurt am Main, Fed. Rep. of Germany

[21] Appl. No.: 592,579

[22] Filed: Oct. 4, 1990

[30] Foreign Application Priority Data

Oct. 7, 1989 [DE] Fed. Rep. of Germany ....... 3933559

[51] Int. Cl.$^5$ .............................................. C07C 51/58
[52] U.S. Cl. ................................................... 562/860
[58] Field of Search ......................................... 562/860

[56] References Cited

U.S. PATENT DOCUMENTS 2,321,823 6/1943 Kirkbride .......................... 204/163
3,654,358 4/1972 Jeffrey .............................. 260/544

Primary Examiner—José G. Dees
Assistant Examiner—Porfirio Nazario-Gonzalez

[57] ABSTRACT

In the conversion of trichloroethene and tetrachloroethene into dichloroacetyl chloride (DAC) or trichloroacetyl chloride (TAC) by means of oxygen, the reaction mixture is passed several times as a thin film through the reaction zone. The reaction time for achieving a certain conversion is in this way reduced.

In the preparation of DAC, a constant content of acid chloride is established in the reaction mixture by removing some of the mixture and working this up by distillation, while the circulating reaction mixture is simultaneously topped up with fresh trichloroethene.
In this way, side reactions are suppressed and the amount of by-products is reduced.

6 Claims, 2 Drawing Sheets

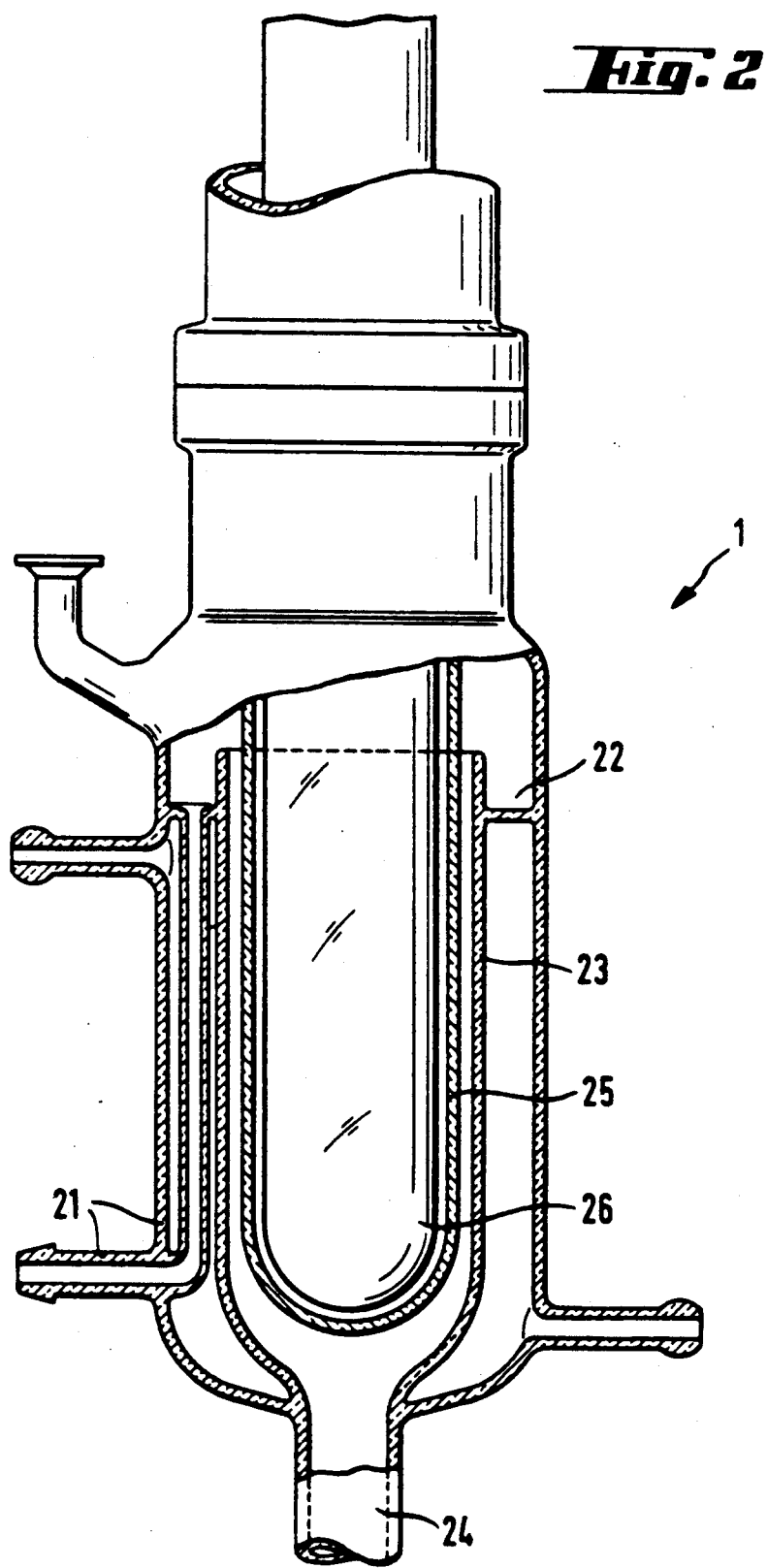

PROCESS FOR THE PREPARATION OF DICHLORO- OR TRICHLOROACETYL CHLORIDE

DESCRIPTION

The invention relates to a gentle process for the preparation of dichloroacetyl chloride or trichloroacetyl chloride.

As is known, dichloro- and trichloroacetyl chloride are obtained by the action of oxygen or oxygen-containing gases, such as, for example, air, on trichloroethene or tetrachloroethene. Usually, these reactions are carried out at a temperature between room temperature and 200° C. under normal pressure or under pressure and are started and kept in progress by agents which form free radicals or by irradiation with light of short wavelength. In addition to the acid chlorides and corresponding epoxides, small amounts of higher-boiling acid chlorides and gaseous by-products, such as, for example, hydrogen chloride, carbon monoxide and phosgene, are formed in these reactions.

The epoxide formed can be rearranged into the acid chloride by addition of nitrogen bases (compare German Patent 2,533,181, German Patent 2,050,562 and German Patent 1,568,547).

The disadvantage of the known processes is that the reaction times are too long. In a conventional oxidation batch with 4,000 kg of trichloroethene, which requires about 60 hours, 99.7% of the trichloroethene being oxidized about 80% of the trichloroethene has already been converted into dichloroacetyl chloride or trichloroethene epoxide after about 30 hours. A further 30 hours are required for oxidation of the remaining 20%. Dichloroacetyl chloride is degraded into undesirable byproducts, such as, for example, phosgene, by this longlasting oxidation.

The object was therefore to discover a process for the preparation of dichloroacetyl chloride or trichloroacetyl chloride which can be carried out in a shorter time.

It has been found that the object can be achieved if the oxidation of the trichloroethene or tetrachloroethene is carried out in a thin layer.

The invention thus relates to a process for the continuous preparation of dichloro- or trichloroacetyl chloride by reaction of trichloroethene or tetrachloroethene with oxygen in the liquid phase under irradiation with light of short wavelength at a temperature of 70 to 140° C. under a pressure of 1 to 20 bar, which comprises passing the starting substance in a thin film through the reaction zone, letting off the waste gas periodically at a frequency such that the pressure variations in the apparatus do not exceed about 10% and keeping the oxygen essentially under static pressure.

BRIEF DESCRIPTION OF THE DRAWINGS

FIG. 2 is a front elevational view, with parts broken away, of a type of falling film photoreactor device which can be used in the apparatus illustrated in FIG. 1.

DETAILED DESCRIPTION

Figure 1:
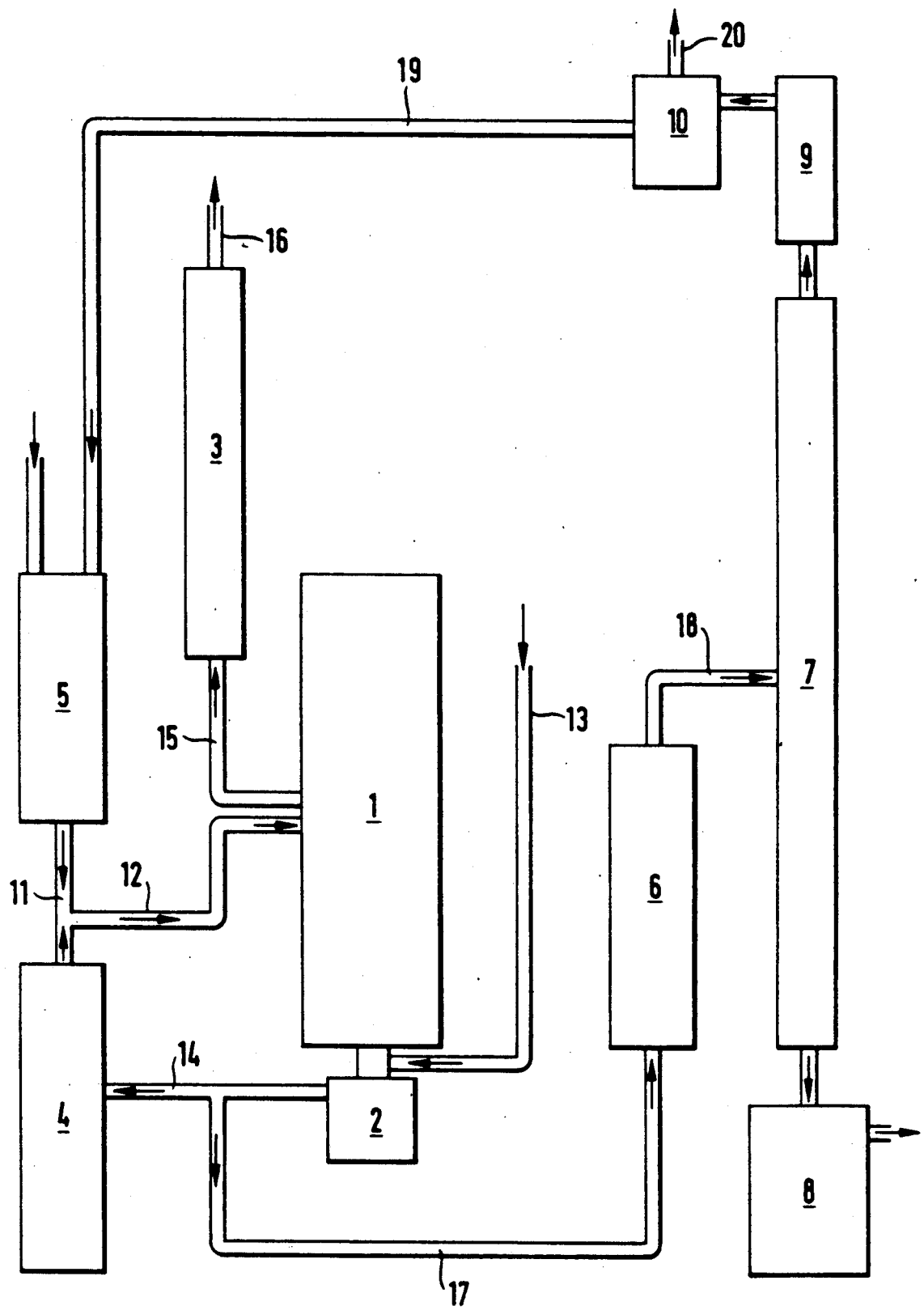
FIG. 1 is a schematic representation of a preferred type of apparatus suitable for carrying out the process of this invention.

The process according to the invention is carried out in an installation which, according to FIG. 1, consists of a falling film photoreactor (1) with a circulating pump (2), a waste gas cooler (3), a buffer vessel (4) and a reservoir vessel (5). If trichloroethene is to be converted into dichloroacetyl chloride, a preheater (6), a distillation column (7), a receiver (8) for DAC., a reflux condenser (9) and a receiver (10) for trichloroethene are also included for separating off the acid chloride.

Trichloroethene or tetrachloroethene is fed to the installation via the reservoir vessel (5). From there, the chloroolefin passes via lines (11) and (12) into the falling film photoreactor (1), where it is passed as a thin film through the reaction zone and reacted there, while being exposed to a UV light source, with oxygen which is fed in through line (13). The reaction mixture collects in the circulating pump (2) and is conveyed from this into the buffer vessel (4), from where it can pass through line (12) back to the reactor (1). Gases formed during the reaction escape through line (15) and are separated from the entrained liquid in the waste gas cooler (3). They pass via line (16) to the waste gas purification.

In the preparation of dichloroacetyl chloride, some of the reaction mixture is diverted through line (17), heated in the preheater (6) and fed through line (18) to the distillation column (7). The higher-boiling dichloroacetyl chloride collects in the receiver (8), and the trichloroethene of lower boiling point is condensed in the condenser (9) and collects in the receiver (10). From here, the trichloroethene recovered runs through line (19) into the reservoir vessel (5), whilst the waste gases leave the installation through line (20).

In the falling film photoreactor, the chloroolefin or the reaction mixture passed in circulation flows as a thin film on the inside of a cylindrical tube and is temperature-controlled from the outside of this tube. Inside the tube is one or more UV light sources in a protective tube—not in contact with the reactants. The reaction temperature is 70 to 140, preferably 70 to 110° C..

The reaction is carried out under an oxygen pressure of 1 to 20 bar, preferably 1 to 4 bar. During the reaction, oxygen does not flow continuously through the reactor, but the waste gas is periodically let off at a frequency such that the pressure variations in the apparatus do not exceed about 10%. The oxygen escaping with the waste gas is replaced here.

The rearrangement of the epoxides likewise formed during the oxidation into the acid chlorides in the presence of organic nitrogen bases or salts thereof is carried out outside the oxidation zone.

To prevent side reactions, for example by further oxidation of the acid chloride or epoxide formed, the reaction mixture is passed in circulation and a constant acid chloride content is established in the reaction mixture by removing 10 to 20% per hour and by adding fresh trichloroethene or tetrachloroethene. This content is 40 to 80, preferably 60 to 70% of acid chloride, based on the reaction mixture. In the continuous preparation of dichloroacetyl chloride, the portion of reaction mixture removed is fed to a continuous distillation. The higher-boiling component, in this case 98 to 99% pure dichloroacetyl chloride, collects in the bottom of the column and the low-boiling components, including the trichloroethene, are distilled off over the top. Fresh trichloroethene is added to the trichloroethene separated off during the distillation, and this mixture is fed back to the oxidation circulation.

Tetrachloroethene is oxidized to trichloroacetyl chloride in an analogous manner. Because the boiling point of tetrachloroethene is only 2° C. higher than that of trichloroacetyl chloride, continuous separation by distillation is not possible. It is therefore advisable to dispense with purification of the trichloroacetyl chloride, if appropriate, and to continue directly with its further processing (for example esterification).

The reaction time is effectively shortened and the amount of by-products obtained reduced by the process according to the invention.

The examples which follow are intended to illustrate the invention in more detail.

EXAMPLE 1

The experiments were carried out in a falling film photoreactor according to Prof. de Meijere. The essential features of this reactor are shown in FIG. 2. The reaction mixture passes through the tube (21) into the reactor, fills the circulation channel (22) and flows on the inside of the cylindrical tube (23) as a thin film through the lower connecting piece (24) to the circulating pump, which is not shown. The protective tube (25) contains a UV light source (26) with cooling jacket. Such reactors are commercially available from specialist dealers.

The reactor was provided with a reservoir vessel for the reaction mixture, in which the epoxide was rearranged with pyridine, a dropping funnel for the starting material and an intensive cooler. The intensive cooler was provided with a mercury seal to adjust the pressure. A TQ 150 mercury high pressure lamp, which is also commercially available, was used as the UV light source. The mercury high pressure lamp was contained in a quartz immersion tube and was cooled with a stream of nitrogen gas. For the experiments, in each case the starting material was introduced into the apparatus, the circulating pump was switched on and the apparatus was heated up via the thermostat. When the reaction temperature was reached, the UV lamp was switched on and oxygen was passed over the film in countercurrent by means of a frit. Under normal pressure, the stream of oxygen, which was charged with HCl, CO and phosgene, was removed directly by the intensive cooler and disposed of. If the reaction was carried out under pressure, the intensive cooler was followed by a mercury seal with which it was possible to establish oxygen pressures of 0.5 to 0.75 bar. To regenerate the oxygen, the increased pressure was adjusted on the gas bottle so that slight blowing out occurred in the intensive cooler.

At the start, the reaction mixture was passed in circulation up to a certain acid chloride content.

In continuous operation in the case of DAC. preparation, some of the reaction mixture was removed from the circulation and fed to continuous distillation. 90 mg of pyridine (0.006%) were added to 1,612 g of trichloroethene and the oxidation was carried out at a temperature of 80° C. under an overall pressure of 1.5 bar. The decrease in the trichloroethene and the increase in the reaction products was monitored by gas chromatography. After about 6.5 hours, the trichloroethene content was 0.4%. The contents of dichloroacetyl chloride and trichloroethylene oxide initially rose linearly, increased less and less after about 5 hours and found a limit value. The total yield of DAC. and epoxide was 93%. The results of the analysis by gas chromatography are summarized in Table 1:

TABLE 1

| Reaction time (hours) | Trichloroethene (%) | DAC (%) | Epoxide (%) |
|---|---|---|---|
| 1 | 82 | 14 | 4 |
| 2 | 61 | 28 | 6 |
| 3 | 42 | 42 | 9 |
| 4 | 23 | 57 | 12 |
| 5 | 9.5 | 70 | 15 |
| 6 | 2 | 80 | 11 |
| 7 | — | 86 | 7 |

EXAMPLES 2 to 4

In each case 90 mg of pyridine (0.006%) were added to 1,612 g of trichloroethene and the oxidation was carried out at 73° C. under various pressures in the falling film photoreactor as in Example 1. As expected, the rate of reaction also rose under a higher pressure. The DAC content initially rose linearly up to a DAC content of about 70%. Thereafter, the additional increase lessened and the content approached an upper limit value which was about 80–85% under all pressures.

The results of the analysis by gas chromatography are shown in Table 2:

TABLE 2

| Reaction time (hours) | DAC content in % at 73° C. under various pressures | | |
|---|---|---|---|
|  | 1 bar | 1.5 bar | 1.75 bar |
| 1 | 11 | 15 | 18 |
| 2 | 22 | 29 | 34 |
| 3 | 33 | 42 | 51 |
| 4 | 45 | 57 | 68 |
| 5 | 55 | 70 | 80 |
| 6 | 66 | 79 | 85 |
| 7 | 77 | 84 | 86 |
| 8 | 84 | 86 | — |
| 9 | 86 | — | — |

EXAMPLE 5

3,500 g of trichloroethene were oxidized continuously in a falling film photoreactor in accordance with Example 1 up to a DAC content of 65%. The epoxide was rearranged continuously by subsequent addition of 200 mg of pyridine (0.006%). Some of the reaction mixture was removed and replaced by fresh trichloroethene, and was passed to continuous distillation. Taking into account the portion which remained in the apparatus and the trichloroethene recycled, a yield of DAC of 95% was achieved.

EXAMPLE 6

1,631 g of tetrachloroethene were oxidized analogously to Example 1 at 110° C. under a pressure of 1.75 bar in a falling film photoreactor.

The TAC increase was monitored by gas chromatography and the tetrachloroethene decrease was monitored by IR spectrography. The oxidation was continued until no further TAC increase took place. In this reaction, a residual content of 3% of tetrachloroethene remained in the TAC and could not be decreased further by further oxidation.

The results of the analysis of the oxidation by gas chromatography are shown in Table 3:

TABLE 3

| Reaction time (hours) | Tetrachloroethene (%) | TAC (%) |
| --- | --- | --- |
| 1 | 80 | 25 |
| 2 | 62 | 45 |
| 3 | 46 | 60 |
| 4 | 32 | 72 |
| 5 | 20 | 82 |
| 6 | 9 | 91 |
| 7 | 3 | — |

Because of the small difference between the boiling points of the tetrachloroethene and the trichloroacetyl chloride, separation by distillation is possible only with very great expenditure. However, the crude acid chloride can be further processed directly, for example to the esters, which can be separated more easily from the tetrachloroethene.

COMPARISON EXPERIMENT 1,612 g of trichloroethene containing 90 mg of pyridine were oxidized in a four-necked flask, fitted with a stirrer, thermometer, reflux condenser and gas inlet tube, while irradiating with UV light and passing through oxygen (normal pressure) at 73° C.

The reaction was monitored by gas chromatography:

| Reaction time (hours) | Trichloroethene (%) | DAC (%) | Epoxide (%) |
| --- | --- | --- | --- |
| 17 | 1.0 | 70.9 | 27.0 |
| 18.5 | 0.04 | 73.1 | 25.6 |

We claim:

1. A process for the continuous preparation of dichloro- or trichloroacetyl chloride by reaction of trichloroethene or tetrachloroethene with oxygen in the liquid phase under irradiation with light of short wavelength at a temperature of 70 to 140° C. under a pressure of 1 to 20 bar, which comprises passing the starting substance in a thin film through the reaction zone, letting off the waste gas periodically at a frequency such that the pressure variations in the apparatus do not exceed about 10% and keeping the oxygen essentially under static pressure.

2. The process as claimed in claim 1, wherein, for continuous preparation of dichloroacetyl chloride, a content of acid chloride in the reaction mixture in the range from 40 to 80% by weight, based on the total amount, is maintained by removing 10 to 20% of the reaction mixture per hour, and working this up by fractional distillation and topping up the reaction mixture with fresh trichloroethene.

3. The process as claimed in claim 1, wherein the thin film in the reaction zone flows through a falling film photoreactor.

4. The process as claimed in claim 2, wherein the content of acid chloride maintained in the reaction mixture is in the range from 60 to 70%.

5. The process as claimed in claim 1, wherein trichloroethylene is reacted with oxygen to prepare dichloroacetyl chloride, which is recovered in a purity of at least 98% by continuous distillation.

6. The process as claimed in claim 1, wherein trichloroacetyl chloride, and the resulting trichloroacetyl chloride is utilized directly in an esterification reaction.

* * * * *